(12) United States Patent
Johnson

(10) Patent No.: US 8,518,349 B2
(45) Date of Patent: Aug. 27, 2013

(54) USE OF AUTOLOGOUS SEDIMENT FROM FLUID ASPIRATES AS VEHICLES FOR DRUG DELIVERY

(76) Inventor: Lanny Johnson, Frankfort, MI (US)

( * ) Notice: Subject to any disclaimer, the term of this patent is extended or adjusted under 35 U.S.C. 154(b) by 0 days.

(21) Appl. No.: 13/448,832

(22) Filed: Apr. 17, 2012

(65) Prior Publication Data

US 2012/0203167 A1 Aug. 9, 2012

Related U.S. Application Data

(63) Continuation-in-part of application No. 13/049,802, filed on Mar. 16, 2011, which is a continuation of application No. 11/518,800, filed on Sep. 11, 2006, now Pat. No. 7,927,630.

(60) Provisional application No. 60/716,064, filed on Sep. 12, 2005.

(51) Int. Cl.
  *B01L 3/14* (2006.01)
  *G01N 21/00* (2006.01)
  *G01N 31/00* (2006.01)
  *G01N 33/00* (2006.01)
  *B01L 9/00* (2006.01)

(52) U.S. Cl.
  USPC ............... 422/549; 422/64; 422/67; 422/561

(58) Field of Classification Search
  USPC ................. 600/576; 422/57, 69, 549
  See application file for complete search history.

(56) References Cited

U.S. PATENT DOCUMENTS

| 3,512,940 | A | * | 5/1970 | Shapiro ..................... 422/535 |
| 3,767,085 | A | * | 10/1973 | Cannon et al. ................. 222/82 |
| 4,828,716 | A | * | 5/1989 | McEwen et al. .............. 210/740 |
| 5,004,681 | A | | 4/1991 | Boyse et al. |
| 5,192,553 | A | | 3/1993 | Boyse et al. |
| 5,197,985 | A | | 3/1993 | Caplan et al. |
| 5,226,914 | A | | 7/1993 | Caplan et al. |
| 5,811,061 | A | | 9/1998 | Martinson et al. |
| 5,811,094 | A | | 9/1998 | Caplan et al. |
| 5,842,477 | A | | 12/1998 | Naughton et al. |

(Continued)

OTHER PUBLICATIONS

Centrifugation Handout, http://www.tulane.edu/~wiser/methods/handouts/class/06_centrif.pdf, accessed Apr. 18, 2012. pp. 1-5.

(Continued)

*Primary Examiner* — Jill Warden
*Assistant Examiner* — Julie Tavares
(74) *Attorney, Agent, or Firm* — Michael J. Gallagher; David J. Dawsey; Gallagher & Dawsey Co. LPA

(57) ABSTRACT

A filtration syringe having at least a first and second chamber separated by a fluid permeable membrane, which may be selectively permeable to solids of a certain size, allows aspirated particle-filled fluid to be filtered within the syringe. A centrifuge tube apparatus is also provided for centrifuging a sample collected in a syringe, the apparatus comprising: a syringe comprising at one end a narrowed outlet and means for connection to a needle and at the opposing end a partially inserted syringe plunger; and a syringe holder having an interior for accepting the syringe, wherein the interior comprises at least one ledge for resting the syringe in an inverted position within the holder to prevent further insertion of the plunger during centrifugation, further wherein the syringe holder is sized for insertion in a centrifuge rotor.

17 Claims, 5 Drawing Sheets

(56) References Cited

U.S. PATENT DOCUMENTS

| | | | |
|---|---|---|---|
| 5,908,784 | A | 6/1999 | Johnstone et al. |
| 6,080,194 | A | 6/2000 | Pachence et al. |
| 6,174,333 | B1 | 1/2001 | Kadiyala et al. |
| 6,387,369 | B1 | 5/2002 | Pittenger et al. |
| 6,461,645 | B1 | 10/2002 | Boyse et al. |
| 6,569,427 | B1 | 5/2003 | Boyse et al. |
| 6,602,294 | B1 | 8/2003 | Sittinger et al. |
| 6,605,275 | B1 | 8/2003 | Boyse et al. |
| 6,815,416 | B2 | 11/2004 | Carney et al. |
| 7,195,606 | B2 * | 3/2007 | Ballin .................. 604/6.01 |
| 7,442,389 | B2 | 10/2008 | Quelle et al. |
| 7,776,010 | B2 * | 8/2010 | Jessop et al. ............ 604/87 |
| 2002/0122790 | A1 | 9/2002 | Hunziker |
| 2003/0130250 | A1 | 7/2003 | Bridger et al. |
| 2003/0173284 | A1 * | 9/2003 | Baker .................. 210/321.6 |
| 2004/0028717 | A1 | 2/2004 | Sittinger et al. |
| 2005/0177100 | A1 * | 8/2005 | Harper et al. ............ 604/89 |
| 2009/0043282 | A1 * | 2/2009 | Hughes et al. .......... 604/518 |
| 2011/0002904 | A1 * | 1/2011 | Johnson ................ 424/93.73 |

OTHER PUBLICATIONS

Chen et al, Mesenchymal stem cells on arthritic diseases, Arthritis Research and Therapy, 2008;10(5):223.

Crawford et al., Synovial Fluid Stem Cells: A Potential Cell Source for Cartilage Tissue Engineering,European Cells and Materials, vol. 16 Suppl. 2, 2008, p. 41.

De Bari et al, Multipotent Mesenchymal Stem Cells From Adult Human Synovial Membrane, Arthritis & Rheumatism. 2001; vol. 44 No. 8, pp. 1928-1942.

Jones et al., Enumeration and Phenotypic Characterization of Synovial Fluid Multipotential Mesenchymal Progenitor Cells in Inflammatory and Degenerative Arthritis,Arthritis & Rheumatism. 2004; vol. 50 No. 3, pp. 817-827.

Jones et al., Synovial Fluid Mesenchymal Stem Cells in Health and Early Osteoarthritis, Arthritis & Rheumatism. 2008; vol. 58, No. 6, pp. 1731-1740.

McGonagle et al., A Potential Role for Synovial Fluid Mesenchymal Stem Cells in Ligament Regeneration, Rheumatology. 2008; vol. 47, No. 8, pp. 1114-1116.

Morito et al., Synovial Fluid-derived Mesenchymal Stem Cells Increase After Intra-articular Ligament Injury in Humans, Rheumatology. 2008; vol. 47, No. 8, pp. 1137-1143.

Pei et al.,Engineering of Functional Cartilage Tissue Using Stem Cells from Synovial Lining, Clinical Orthopaedics and Related Research. 2008; 466(8):1880-1889.

De Bari et al., Failure of In Vitro—Differentiated Mesenchymal Stem Cells From the Synovial Membrane to Form Ectopic Stable Cartilage In Vivo ,Arthritis & Rheumatism. 2004; vol. 50, No. 1, pp. 142-150.

* cited by examiner

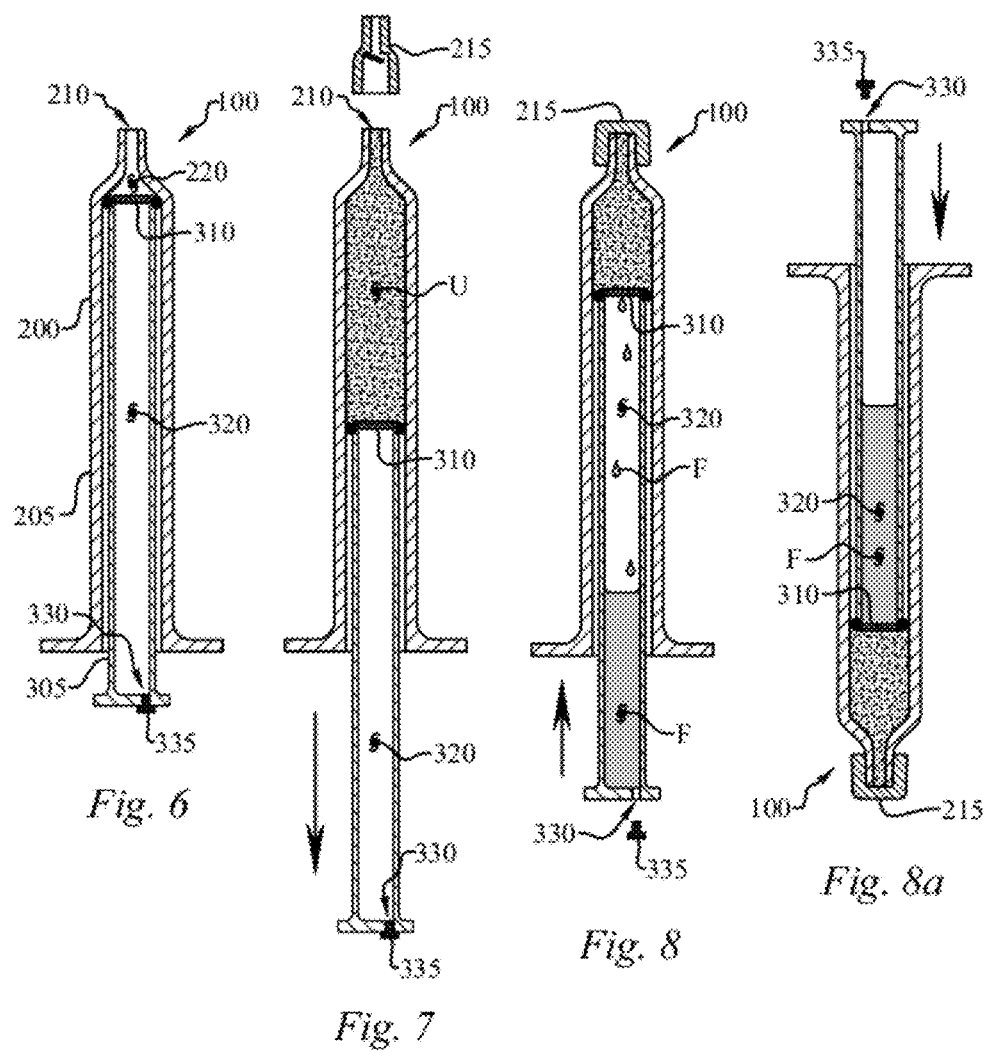

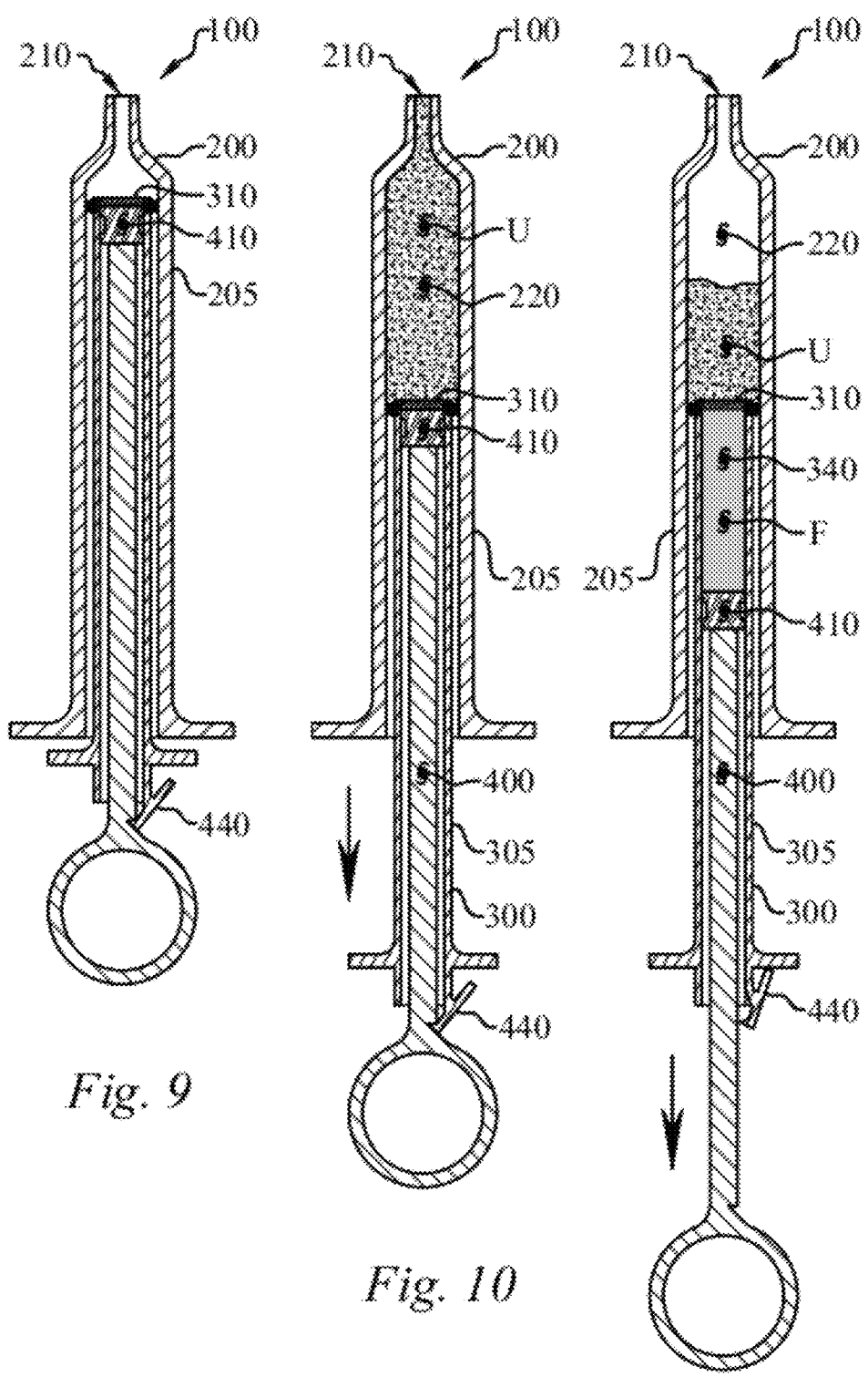

USE OF AUTOLOGOUS SEDIMENT FROM FLUID ASPIRATES AS VEHICLES FOR DRUG DELIVERY

CROSS REFERENCE TO RELATED APPLICATIONS

This invention is a continuation in part of U.S. patent application Ser. No. 13/049,802, filed Mar. 16, 2011; which is a continuation of U.S. patent application Ser. No. 11/518,800, filed Sep. 11, 2006; which itself claims priority to U.S. patent application Ser. No. 60/716,064 filed on Sep. 12, 2005, now expired.

FIELD OF THE INVENTION

The present invention relates generally to vehicles for delivering one or more factors such as cytokines, bone morphogenetic proteins (BMPs), pharmaceutical drugs and gene vectors. Specifically, the present invention relates to the use of autologous sediment from fluid aspirates as delivery vehicles.

BACKGROUND OF THE INVENTION

Solutions, suspensions and emulsions have been used throughout the years as vehicles for delivery of the active ingredients of pharmaceutical drugs. These delivery vehicles do not allow for the maintenance of effective dosage levels of the active ingredients in the bloodstream. Sustaining a dosage of a therapeutic factor may require multiple injections, which can increase the likelihood of infection. Therapeutic factors such as pharmaceutical drugs and recombinant proteins often require controlled and sustained release at specific target tissues to be safe and effective. If there is a narrow difference between therapeutic and toxic levels (therapeutic index) of a drug it will require strict compliance to an injection schedule by the patient. Additionally, cytokines such as IL-2 have a danger of systemic toxicity. IL-2 has useful local therapeutic potential, but systemically it can cause vascular shock and pulmonary edema. Another concern is that therapeutic peptides have a very short half-life, so that targeted, controlled and sustained release is important for their effectiveness.

Recent advancements in the field of delivery vehicles allow for the controlled and sustained delivery of drugs. The advancements include such technologies as osmotic pumps, liposomes, dendrimers, and microencapsulation in biodegradable polymers such as microparticles, microspheres or nanoparticles. U.S. Pat. No. 4,489,055 to Couvreur et al., for example, describes biodegradable particles of alkyl-cyano-acrylate containing a biologically active substance. Particles comprised of various polymers and copolymers, such as PLG [poly(lactide-co-glycolide)], PCL [poly(,-caprolactone)], PLA [poly(L-lactic acid)] and PBLA [poly($\beta$-benzyl-L-aspartate)] have been described (M. Ravi Kumar J. Pharm. Parmaceut. Sci. 3(2): 234-258, 2000). Alginate (including calcium alginate beads encapsulated with poly-L lysine) and chitosan have both been used extensively to create microcapsules and microspheres. Maintaining a minimal inflammatory response to the vehicle is important in any design for a delivery vehicle that is to be placed within the human body. Other advancements which allow for targeted and controlled release of factors include gene therapy. The use of a patient's own cells to carry the factor avoids some of the issues relating to immune rejection, since the drug vehicle is autologous.

One difficult tissue of the body to target with drugs or other factors is the synovium. Some have described the use of synovial fluid constituents for injection. For example, U.S. Pat. No. 4,141,973 to Balazs describe a purified high molecular weight hyaluronic acid fraction extracted from animal tissues for injection into a joint. U.S. Pat. No. 5,079,236 to Drizen et al. describe a purified high molecular weight hyaluronic acid fraction for treatment of joint disease in animals. HYALGAN sodium hyaluronate (Sanofi-Synthelabo Inc, New York, N.Y.) is a purified hyaluronate from rooster combs for injection into knee joints for the purpose of pain relief. U.S. Pat. No. 6,699,471 B2 and U.S. Patent Application Publication No. 2004/0142465 A1 to Radice et al. describe injectable compositions having hyaluronic acid derivatives and cells such as chondrocytes for the treatment of soft tissues. CARTICEL autologous cultured chondrocytes (Genzyme, Cambridge, Mass.) are presently used for the repair of articular cartilage defects caused by acute or repetitive trauma. The therapeutic chondrocytes are derived from an in vitro expansion of autologous chondrocytes harvested from the normal, femoral articular cartilage of the patient to be treated. The cells are isolated and expanded, then implanted into the articular cartilage defect beneath an autologous periosteal flap sutured over the cartilage defect.

The synovium and synovial fluid in patients with rheumatoid arthritis are known to have upregulated proinflammatory cytokines Anti-inflammatory agents are activated in the disease, but do not counter the proinflammatory response. Interferon-E-$\beta$ (IFN-$\beta$) is a natural anti-inflammatory, because it downregulates proinflammatory cytokines such as IL 1$\beta$ and tumor necrosis factor-$\alpha$. (TNF-$\alpha$t while also increasing the IL-1 receptor antagonist in synoviocytes. Van Holten et al. (Arth. Res., vol. 6, no. 3) teach treatment in an animal model of rheumatoid arthritis using intraperitoneal injections of IFN-$\beta$ to ameliorate the arthritis. However, this requires systemic treatment with the IFN-$\beta$. Locally targeted therapy would be desirable. Bandara et al., Proc. Natl. Acad. Sci, USA, vol. 90, pp. 107641-10768 (1993) and Makarov et al., Proc. Natl. Acad, Sci, USA, vol. 93, pp. 402-406 (1996) take another approach by transducing synoviocytes with a cDNA so as to express the interleukin-1 receptor-antagonist (IL-lra) protein. Del Vecchio et al. (Arth. Res., vol. 3, no. 4) teach approaches to enhance the transduction of human synoviocytes with the interleukin-1 receptor-antagonist (IL-lra) cDNA. The ex vivo transfer of genes for delivering genes to the synovial lining of joints seems to selectively target type B synoviocytes, In vivo gene delivery by intra-articular injection of adenovirus vectors apparently transduces leukocytes and both type A and B synoviocytes (Evans, Arth, Res., vol. 1 no. 1, pp. 21-24, 1999). Research by Ghivizzani et al. (Proc Natl Acad Sci, USA 1998, 95:4613-4618) shows a contralateral effect of in vivo gene delivery, which suggests that transduced leukocytes have the capacity to traffic between joints.

While the related art teach various drug delivery vehicles which give controlled and sustained release, and while some related art utilize synovial fluid constituents such as hyaluronic acid for the treatment of joint disease, there still exists a need for improved delivery vehicles for factors, such as drugs, gene vectors and cytokines which allow for targeted, controlled and sustained release of the factors.

OBJECTS OF THE INVENTION

Therefore, it is an object of the present invention to provide a means to deliver one or more factors to a patient.

It is further an object of the present invention to provide a means to deliver of one or more factors to the patient utilizing autologous material so as to minimize any inflammatory response.

These and other objects will become increasingly apparent by reference to the following description.

SUMMARY OF THE INVENTION

The present invention provides a method of delivering one or more factors to a patient which comprises collecting a fluid aspirate from the patient, in some embodiments centrifuging the fluid aspirate to provide a supernatant and a sedimented material, separating the supernatant from the sedimented material, immersing the sedimented material in a solution comprising one or more factors so as to provide a treated sediment, and introducing the treated sediment to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the sedimented material after separating, and before immersing, is examined and treated to remove unwanted components, to supply wanted components or both.

The present invention provides a method of delivering one or more factors to a patient which comprises collecting a fluid aspirate from the patient, in some embodiments centrifuging the fluid aspirate to provide a supernatant and a sedimented material, separating the supernatant from the sedimented material, immersing the sedimented material in a solution comprising one or more factors, pressurizing the sedimented material in the solution comprising one or more factors so as to provide a treated sediment, and introducing the treated sediment to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the sedimented material after separating, and before immersing, is examined and treated to remove unwanted components, to supply wanted components or both.

The present invention provides a method of delivering one or more factors to a patient which comprises collecting a fluid aspirate from the patient, in some embodiments centrifuging the collected fluid aspirate to provide a supernatant and sedimented material, separating the supernatant from the sedimented material, immersing the sedimented material in a solution comprising one or more factors to provide a treated sediment, placing the treated sediment into a biologically compatible medium, and introducing the treated sediment and biologically compatible medium into a tissue of the patient so as to deliver the one or more factors to the patient.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the sedimented material after separating, and before immersing, is examined and treated to remove unwanted components, to supply wanted components or both.

The present invention provides a method of delivering one or more factors to a patient which comprises collecting a fluid aspirate from the patient, in some embodiments centrifuging the collected fluid aspirate to provide a supernatant and sedimented material, separating the supernatant from the sedimented material, immersing the sedimented material in a solution comprising one or more factors, pressurizing the sedimented material in the solution comprising one or more factors so as to provide a treated sediment, placing the treated sediment into a biologically compatible medium, and introducing the treated sediment and biologically compatible medium into a tissue of the patient so as to deliver the one or more factors to the patient.

In further embodiments, a filtration syringe is provided such that sediment filled fluid may be filtered into a sediment-free component.

The present invention provides a method of delivering one or more factors to a patient which comprises collecting a fluid aspirate from the patient, centrifuging the fluid aspirate to provide a supernatant and a sedimented material, separating the supernatant from the sedimented material, purifying one or more components of the sedimented material, immersing the one or more components in a solution comprising one or more factors so as to provide a treated vehicle, and introducing the treated vehicle to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the purified components of the purification step are examined to determine the purity of the components prior to immersing.

The present invention provides a method of delivering one or more factors to a patient which comprises collecting a fluid aspirate from the patient, in some embodiments centrifuging the fluid aspirate to provide a supernatant and a sedimented material, separating the supernatant from the sedimented material, purifying one or more components of the sedimented material, immersing the one or more components in a solution comprising one or more factors, pressurizing the one or more components in the solution comprising one or more factors so as to provide a treated vehicle, and introducing the treated vehicle to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the treated vehicle is examined in the step of pressurizing, before being introduced into the patient.

The present invention provides a method of delivering one or more factors to a patient which comprises collecting a fluid aspirate from the patient, in some embodiments centrifuging the collected fluid aspirate to provide a supernatant and sedimented material, separating the supernatant from the sedimented material, purifying one or more components of the sedimented material, immersing the one or more components in a solution comprising one or more factors, placing the one or more components in the solution comprising one or more factors into a biologically compatible medium so as to provide a treated vehicle, and introducing the treated vehicle into a tissue of the patient so as to deliver the, one or more factors to the patient.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the purified components of the purifying step are examined to determine the purity of the components prior to the immersing step.

The present invention provides a method of delivering one or more factors to a patient which comprises collecting a fluid aspirate from the patient, in some embodiments centrifuging the collected fluid aspirate to provide a supernatant and sedimented material, separating the supernatant from the sedimented material, purifying a one or more components of the sedimented material, immersing the one or more components in a solution comprising one or more factors, pressurizing the one or more components in the solution comprising one or more factors, placing the one or more components in the solution comprising one or more factors into a biologically compatible medium so as to provide a treated vehicle, and introducing the treated vehicle into a tissue of the patient so as to deliver the one or more factors to the patient. In still further embodiments the purified components of the purifying step are examined to determine the purity of the components prior to the immersing step.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof.

The present invention provides a method of delivering one or more factors to a patient which comprises: (a) collecting a fluid aspirate from the patient; (b) in some embodiments centrifuging the fluid aspirate to provide a supernatant and a sedimented material; and (c) separating the supernatant from the sedimented material; (d) providing one or more factors to the supernatant so as to provide a mixture; and (e) injecting the mixture into the patient to deliver the one or more factors to the patient. In further embodiments the fluid aspirate is synovial joint effusion, pleural effusion, pericardial effusion, or ascites. In still further embodiments the one or more factors are injected to repair cartilage in a joint. In still further embodiments the one or more factors are a cytokine. In still further embodiments the one or more factors are bone morphogenetic proteins (BMPs). In still further embodiments the one or more factors are a pharmaceutical drug. In still further embodiments the one or more factors are a gene vector.

The present invention provides a method of delivering one or more factors to a patient which comprises: (a) collecting a fluid aspirate from the patient; (b) in some embodiments centrifuging the collected fluid aspirate to provide a supernatant and sedimented material; and (c) separating the supernatant from the sedimented material; (d) placing a biologically compatible medium into the supernatant; (e) providing one or more factors to the supernatant and biologically compatible medium so as to provide a therapeutic mixture; and (f) placing the therapeutic mixture into a tissue of the patient so as to deliver the one or more factors to the patient.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are to repair cartilage in a joint. In still further embodiments the one or more factors are cytokines, bone morphogenetic proteins (BMPs), pharmaceutical drugs, or gene vectors. In still further embodiments the supernatant after step (c) is examined and treated to remove unwanted components.

BRIEF DESCRIPTION OF THE DRAWINGS

FIG. 6 is a side sectional view of a further embodiment of a filtration syringe;

FIG. 7 is a side sectional view of a further embodiment of a filtration syringe;

FIG. 8 is a side sectional view of a further embodiment of a filtration syringe;

FIG. 8a is a side sectional view of the embodiment of FIG. 8 in a vertically reversed spatial orientation;

FIG. 9 is a side sectional view of a further embodiment of a filtration syringe;

FIG. 10 is a side sectional view of a further embodiment of a filtration syringe; and FIG. 11 is a side sectional view of a further embodiment of a filtration syringe.

Figure 1:
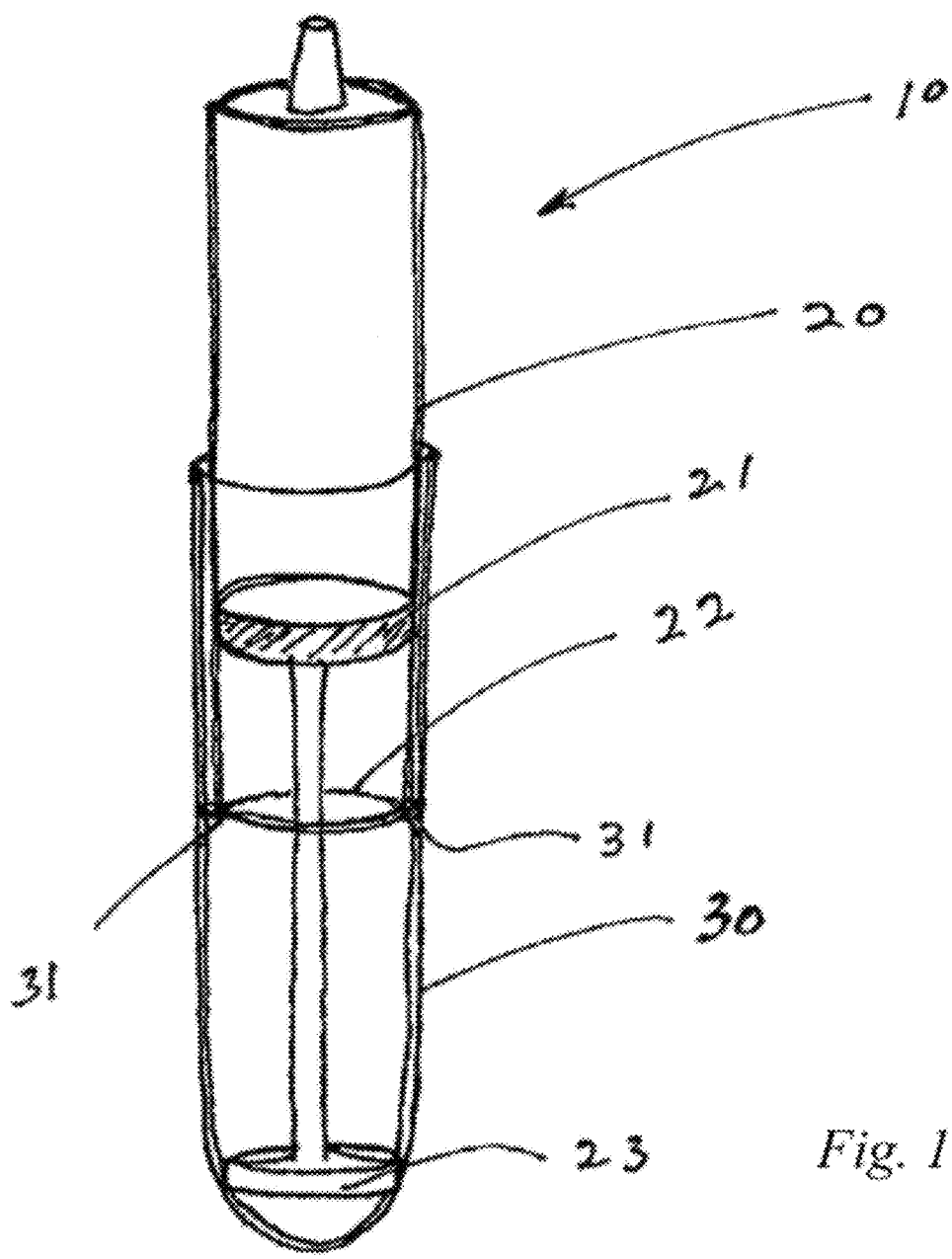
FIG. 1 is a side view of a centrifuge tube having a collection tube.

These drawings are provided to assist in the understanding of the exemplary embodiments of the invention as described in more detail below and should not be construed as unduly limiting the invention. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

Synovium constitutes the lining of synovial joints. It consists of a series of cells covering linings of fat and vascularity. The cells secrete synovial fluid. These cells naturally shed and can be found in small numbers in synovial fluid. In joint inflammation the lining proliferates into fingerlike projections called villi. These finger like projections are lined with synovial cells and filled with fat and vessels. Therefore there are synovial cells, fat cells with potential for some stem cells, fibroblasts, blood with monocytes and lymphocytes plus angioblasts. The latter are there related to the reaction of the synovium and the increased vascularity. It has been reported by Hunziker and Rosenberg that synovium will grow over cartilage and heal a laceration in cartilage (J Bone Joint Surg Am. 1996 May; 78(5):721-33).

Body fluids such as synovial fluid contain a variety of materials that when isolated can serve as vehicles for drug and gene delivery. For example the synovial joint effusion that accompanies degenerative arthritis has a variety of debris. The fluid can be removed by arthrocentesis. The fluid contains cellular and tissue debris that is often visible to the naked eye. When subjected to centrifuging, the material is separated out and collectable from the centrifuge tube. (Johnson, L L. Arthroscopic Surgery Principles and Practice. C. V. Mosby 1986, St. Louis). When joint fluid undergoes centrifugation the sediment has components including, but not limited to white blood cells, red blood cells, synovial cells, synovial fragments, and articular cartilage fragments with and without viable appearing cells.

Protocol: One embodiment of the method involves the separation of the autologous joint fluid tissue debris by centrifuging and discarding the supernatant. The sediment from the centrifugation is saved. Optionally, blood or a fibrin blood clot can be added. The sediment is immersed in one or more factors, for example a drug or gene vector, for up to 30 minutes. The one or more factors is adsorbed over various times onto the various components which make up the sediment. Actuation of pressure on the debris and the factors is one means encompassed by the present invention to increase the saturation of the drug or other factors in the debris. The autologous sediment with adsorbed drug or gene vector is then injected into the patient for the intended purpose. The drug or gene vector is selectively released from each constituent of the sediment at a different rate, according to cell and tissue type, giving a prolonged and even timed release of the drug. In one embodiment shown in FIG. 1, a sterile, disposable centrifuge tube (10) is used for performing the methods of the present invention which can be used during outpatient surgery, or in a hospital surgery operating theater. The centrifuge tube (10) apparatus has a collection tube (20) that doubles as pressure chamber and a delivery syringe and home for the drug or drug combination. In one example, the centrifuge tube (10) apparatus comprises a collection tube (20) that doubles as a delivery syringe which is inverted within a holder (30) during centrifugation. The collection tube (20) rests upon ledges (31) in the holder (30) so that a plunger (21) remains towards an open end (22) of the collection tube (20) during centrifugation. The collection tube (10) can be removed from the holder (30) after separation of the sediment from the fluid. The supernatant can then be removed from the collection tube (20) by pressing the handle (23). The remaining sediment can then be resuspended by shaking or vortexing. Another example of a centrifugation syringe which can be utilized to perform the method of the present invention is disclosed in U.S. Pat. No. 5,577,513 to Van Vlasselaer hereby incorporated herein by reference in its entirety. The delivery instrument could be as simple as a syringe and needle. The material could be delivered in an autogenous fibrin blood clot, via a bioabsorbable sponge, or injected under a patch of autogenous tissue.

One example of this is the treatment of cartilage injury or disease. The injured or degenerative joint has fluid with cells, cell debris, synovium, synovial cells, cartilage matrix, cartilage with matrix and cells. A cytokine such as one of the Bone Morphogenetic Proteins (BMPs) is mixed with sediment. The combination is then placed into the joint with or without a medium such as a bioabsorbable sponge. BMPs are proteins within the transforming growth factor- beta (TGF-c super- family which bind to serine/threonine transmembrane receptors that phosphorylate Smad second messenger family proteins which regulate transcription of various genes. A subfamily of BMPs, called GDFs, are localized in joints during development and therefore may be critical for synovial joint morphogenesim. The BMPs, among other growth factors, can be delivered directly as a protein or via gene vectors. Other examples of sediments from fluid aspirates which can be used to provide vehicles for delivery of factors such as drugs and genes are those obtained from pleural effusion, pericardial effusion and ascites, In another embodiment, the supernatant fluid remaining after centrifugation is utilized. In this embodiment, the particles would be removed and only the lubricant proteins would remain in the synovial fluid. Cartilage debris is thereby removed. The proteins which are in the supernatant are analyzed, and then mixed with one or more factors, for example BMP, and reinjected into the patient. A disposable centrifuge tube (10) such as described previously is used. The syringe can be already coated with one or more factors, such as BMP, when aspirating the surface synovial fluid in the centrifuge tube (10). The contents of the syringe are then injected at a certain time interval. In some embodiments the contents are injected immediately.

Figure 2:
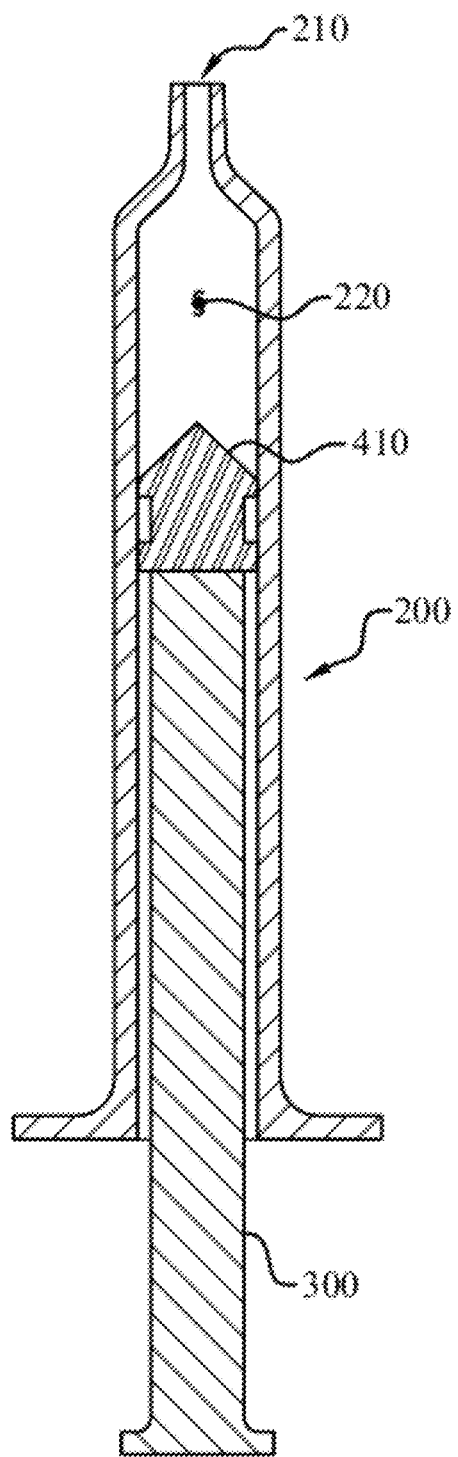
FIG. 2 is a side sectional view of a prior art syringe.

In yet another series of embodiments, in which centrifugation may or may not be either desired or needed, seen well in FIGS. 3-11, a novel filtration syringe (100) may be seen, as compared with the typical prior art syringe seen in FIG. 2. As seen well in FIGS. 3-5, the filtration syringe (100) has a syringe body (200) having a longitudinal axis (A). At least one syringe body sidewall (205) cooperates with an axially disposed movable first plunger body (300) having a fluid filtering barrier comprised of a semi-permeable membrane (310) movable within the syringe body (200) in an axial direction to enclose a first variable chamber (220). This first variable chamber (220) has a first chamber volume in interruptible fluid communication with an external instrumentality (I) through an instrument aperture (210). Typically, the instrument aperture (210) will be attached to a diagnostic instrumentality (I), which may typically be any of a wide variety of hollow needles, as shown for illustration only in FIG. 4, but may also include valves, tubing, or any means by which fluid samples may be collected.

The first movable plunger body (300) has at least one first plunger body sidewall (305) enclosing a second chamber (320) having a second chamber volume. The syringe is capable of filtering particulate filled fluid (U), seen in FIGS. 7-8, because the first variable chamber (220) is in fluid communication with the second chamber (320) by means of the fluid filtering barrier comprised of a semi-permeable membrane (310). This allows the fluid contained within the first variable chamber (220) to transit the fluid filtering barrier (310) into the second chamber (320).

FIGS. 6-8 show the filtration syringe (100) in sequential steps in the collection of particulate-filled fluid. In an initial operation position, seen well in FIG. 6, and with the diagnostic instrumentality there shown removed for simplicity's sake, the first movable plunger body (300) is fully engaged within the first variable chamber (220), such that the first variable chamber volume is at a minimum.

As aspiration begins, as seen well in FIG. 7, the first movable plunger body (300) is partially withdrawn from the first variable chamber (220), such that the first variable chamber volume begins to expand and particulate filled fluid (U) is being drawn into the first variable chamber (220) through the instrument aperture.

At the completion of aspiration, as seen well in FIG. 8, the first movable plunger body (300) is almost maximally withdrawn, but still retained within, the first variable chamber (220). The first variable chamber volume has reached its maximum and particulate filled fluid (U) fills the first variable chamber (220) through the instrument aperture. The particulate filled fluid has begun to transit the fluid filtering barrier comprised of a semi-permeable membrane (310) and begins to fill the second chamber (320) with filtered fluid (F).

Various other features assist this filtration process. The instrument aperture (210) is reversibly occludable by an instrument aperture occluder (215). This allows the first movable plunger body (300) to be moved in a retrograde fashion within the first variable chamber (220), thus increasing the pressure of the particulate filled fluid (U) and speeding filtration. In various different embodiments, the instrument aperture occluder (215) may a check valve, as seen in FIG. 7, or may be a valve allowing alternating bidirectional flow (not illustrated). In other embodiments, as seen in FIGS. 8 and 8a, the instrument aperture occluder (215) may be a removable cap The fluid filtering barrier comprised of a semi-permeable membrane (310) may be selectively filtering to solids of different diameters, in differing embodiments. In some embodiments, the fluid filtering barrier (310) may be filtering to solids passable through a pore size of approximately between 5 and 50 microns. In other embodiments, the fluid filtering barrier (310) may be filtering to solids passable through a pore size of approximately not greater than 50 microns. In yet other embodiments, the fluid filtering barrier (310) may be filtering to solids passable through a pore size of approximately not greater than 35 microns. In yet other embodiments, the fluid filtering barrier (310) may be filtering to solids passable through a pore size of approximately not greater than 22 microns. One skilled in the art will realize that passability through a given pore size is not precisely equivalent to diameter of a solid, as the solid may be deformable through a pore size smaller than its diameter, or, conversely, may be associated with other materials that prevent its passage even through a pore size equal to or larger that the solid diameter. Equally, solids are not uniform in diameter, and may pass or not pass dependent on their spatial orientation.

The filtration syringe (100) may be associated with a wide variety of substances including drugs or other biological adjuncts, especially as may be provided within the first variable chamber (220) and/or the second chamber (320) in the form of coatings, powders or some other adjunct form. Such adjuncts may include, by means of illustration only and not limitation, cytokines, bone morphogenetic proteins (BMPs), pharmaceutical drugs, gene vectors or mixtures thereof. In some embodiments, the first variable chamber (220) and/or the second chamber (320) may be at least partially coated with bone morphogenic protein (BMP). In other embodiments, the first chamber (220) and/or the second chamber (320) may contain bone morphogenic protein (BMP) in either liquid or dry forms. In other embodiments, the first chamber (220) and/or the second chamber (320) may contain a pigment such as an anthocyanin, an anthocyanidin, or a combination of an anthocyanin and an anthocyanidin.

Figures 3, 4, 5:
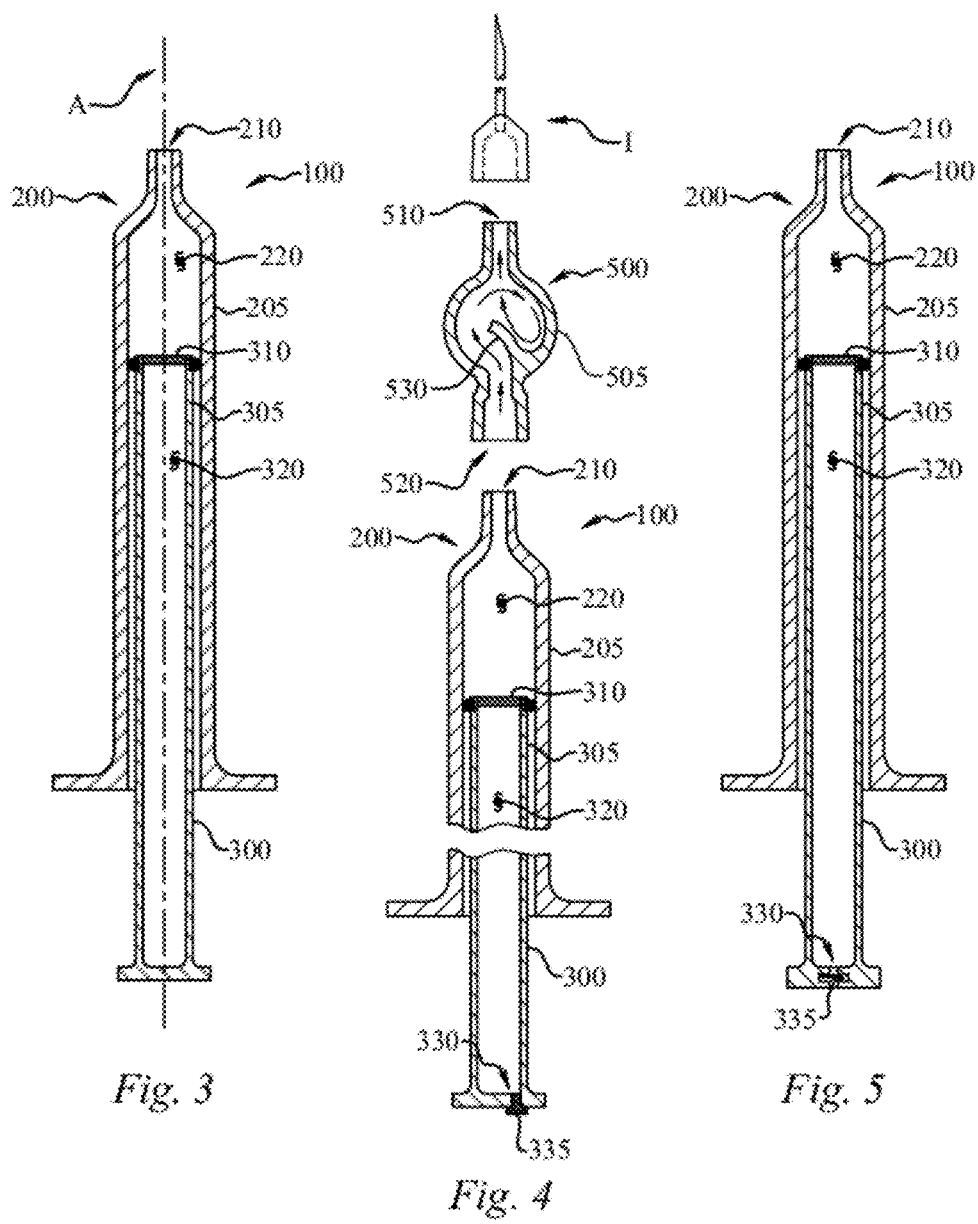
FIG. 3 is a side sectional view of an embodiment of a filtration syringe.
FIG. 4 is a side sectional view of a further embodiment of a filtration syringe, in which arrows are indicated to illustrate, but not to limit, a possible fluid path through a mixing chamber.
FIG. 5 is a side sectional view of a further embodiment of a filtration syringe.

Particularly, but not by any means exclusively, in those embodiments wherein the filtration syringe (100) may incorporate an adjunct such as, by means of example and not limitation only, cytokines, bone morphogenetic proteins (BMPs), pharmaceutical drugs, gene vectors or mixtures thereof, or an anthocyanin and/or anthocyanidin, it may be desirable to make further provision for the mixing of such adjuncts into the aspirated fluid, as seen well in FIG. 4. In some embodiments, the filtration syringe (100) may further include an attachment mixing chamber (500) having at least one mixing chamber sidewall (505) enclosing a mixing chamber volume, the mixing chamber attachable to the filtration syringe at the instrument aperture (210). This mixing chamber (500) may be in fluid communication with the first variable chamber (220) through a mixing chamber—syringe aperture (520) and in fluid communication with an external instrumentality (I) through a mixing chamber—instrument aperture (510). In order to provide enhanced mixing, the mixing chamber sidewall (505) may have at least one laminar flow disrupting feature (530), as seen in FIG. 4. In other embodiments, the laminar flow disrupting feature (530) is expressly not limited to be on the mixing chamber sidewall (505), but may in fact be any configuration of the interior of the mixing chamber (500) that will provide an alteration of fluid flow within the mixing chamber (500) designed to enhance mixing within the chamber.

To further assist in the filtration process, the second chamber (320) may be interruptably vented to an ambient atmosphere through an equalization aperture (330) that is reversibly occludable by an equalization aperture occluder (335), as seen in FIGS. 4-5 and 7-8a. This allows, following inversion of the filtration syringe (100) to avoid spillage, as seen in FIG. 8a, pressure to be vented from the second chamber, thus increasing the pressure gradient between the first variable chamber (220) and the second chamber (320), and promoting fluid transit across the fluid filtering barrier (310).

The movable second plunger body (400) may take various forms in differing embodiments. In some embodiments, the equalization aperture occluder (335) is a valve allowing alternating bidirectional flow, as seen in FIG. 5. In other embodiments, the equalization aperture occluder (335) is a puncturable septum, as seen in FIG. 4, which typically may be punctured with a sharp needle or tip to vent the second chamber (320). The equalization aperture occluder (335) might be removed if the syringe (100) is suitably positioned, as seen in FIG. 8a.

In a further full series of embodiments, as seen in FIGS. 9-11, the second chamber (320) may have an axially disposed movable second plunger body (400). This movable second plunger body (400) may have a fluid impermeable barrier (410), reversibly movable in an axial direction within the first plunger body (400), to enclose a second variable chamber (340) having a second variable chamber volume. Among other advantages, the designs of these embodiments eliminates the need for both an instrument aperture occluder (215) and equalization aperture occluder (335). Fluid may be drawn through the fluid filtering barrier comprised of a semi-permeable membrane (310) into the second variable chamber (340), in a series of steps which are shown, for illustration only, sequentially in FIGS. 9-11.

The axially disposed movable second plunger body (400) may be biased to maintain a reversibly fixed position within the first plunger body (300) by means of a plunger interlock (440), as seen in FIGS. 9-11. The interlock may prevent the second plunger body (400) from being prematurely withdrawn from the first plunger body (300) as seen in FIGS. 9 and 10, until the first variable chamber (220) is adequately filled, as seen in FIG. 11.

As with previous embodiments discussed, the fluid filtering barrier (310) may be selectively filtering to solids of different diameters, in differing embodiments. In some embodiments, the fluid filtering barrier (310) may be filtering to solids passable through a pore size of approximately between 5 and 50 microns. In other embodiments, the fluid filtering barrier (310) may be filtering to solids passable through a pore size of approximately not greater than 50 microns. In yet other embodiments, the fluid filtering barrier (310) may be filtering to solids passable through a pore size of approximately not greater than 35 microns. In yet other embodiments, the fluid filtering barrier comprised of a semi-permeable membrane (310) is filtering to solids passable through a pore size of approximately not greater than 22 microns. One skilled in the art will realize that passability through a given pore size is not precisely equivalent to diameter of a solid, as the solid may be deformable through a pore size smaller than its diameter, or, conversely, may be associated with other materials that prevent its passage even through a pore size equal to or larger that the solid diameter. Equally, solids are not uniform in diameter, and may pass or not pass dependent on their spatial orientation.

Again as with previous embodiments discussed, the filtration syringe (100) may be associated with a wide variety of substances including drugs or other biological adjuncts, especially as may be provided within the first variable chamber (220) and/or second variable chamber (340) in the form of coatings, powders or some other adjunct form. Such adjuncts may include cytokines, bone morphogenetic proteins (BMPs), pharmaceutical drugs, gene vectors or mixtures thereof. In some embodiments, the first variable chamber (220) and/or the second variable chamber (340) may at least partially coated with bone morphogenic protein (BMP). In other embodiments, the first chamber (220) and/or the second variable chamber (340) may contain bone morphogenic protein (BMP) in either liquid or dry forms. In other embodiments, the first chamber (220) and/or the second variable chamber (340) may contain a pigment such as an anthocyanin, an anthocyanidin, or a combination of an anthocyanin and an anthocyanidin.

Particularly, but not by any means exclusively, in those embodiments wherein the filtration syringe (100) may incorporate an adjunct such as, by means of example and not limitation only, cytokines, bone morphogenetic proteins (BMPs), pharmaceutical drugs, gene vectors or mixtures thereof, or an anthocyanin and/or anthocyanidin, it may be desirable to make further provision for the mixing of such adjuncts into the aspirated fluid. In some embodiments, the filtration syringe (100) may further include a mixing chamber (500) having at least one mixing chamber sidewall (505) enclosing a mixing chamber volume, as seen in FIG. 4.

This mixing chamber (500) may be in in fluid communication with the first variable chamber (220) through a mixing chamber—syringe aperture (520) and in fluid communication with an external instrumentality (I) through a mixing chamber—instrument aperture (510). In order to provide enhanced mixing, the mixing chamber sidewall (505) may have at least one laminar flow disrupting feature (530), as seen in FIG. 4. In other embodiments, the laminar flow disrupting feature (530) is expressly not limited to be on the mixing chamber sidewall (305), but may in fact be any configuration of the interior of the mixing chamber (500) that will provide an alteration of fluid flow within the mixing chamber (500) designed to enhance mixing within the chamber.

Optionally, in some embodiments, the precipitated tissues are examined for diagnostic purposes prior to use. Some materials which have been collected may be detrimental to the patient and these unwanted components must be removed, while other materials may be helpful to reintroduce into a patient. For example, certain proteins and or cellular debris may cause an immune response or inflammation in the patient. In some embodiments which utilize the supernatant for introduction into the patient, specific proteins or all proteinaceous material can be extracted or bound before the patient receives the supernatant materials. For diagnostic analysis, the materials can be centrifuged and the precipitates and smears of the supernatant can be examined morphologically and histochemically for their nature and acceptability for purity and subsequent use. The precipitant can be examined including placement in paraffin blocks for histological analysis. Inspection can be by microscopy for crystals, fragments, bacteria, with or without special biological staining to identify the nature of any associated material. The precipitant may be subject to any known bioassay for factors that might, or might not, be desired in the material to be injected.

EXAMPLES

A synovial joint fluid aspirate is to be collected from a knee joint of a patient. The fluid aspirate is then centrifuged to provide a supernatant and a sedimented material. The supernatant is then be removed from the sedimented material and one or more factors such as cytokines and bone morphogenetic proteins (BMPs) are then provided to the supernatant so as to provide a therapeutic mixture. Prior to injecting the mixture into the patient to deliver these factors, the mixture can be tested on alternate knees in a laboratory animal to determine whether the prepared therapeutic mixture is sufficiently clean. Treated versus untreated knees of the laboratory animal can be then compared. If it is determined that the mixture is sufficiently clean, the therapeutic mixture can be then be injected into the knee of the patient which requires treatment.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

What is claimed is:

1. A kit comprising a filtration syringe (100) comprising,
a syringe body (200) having a longitudinal axis (A) and at least one syringe body sidewall (205) cooperating with an axially disposed movable first plunger body (300) having a fluid filtering barrier comprised of a semi-permeable membrane (310) movable within the syringe body (200) in an axial direction to enclose a first variable chamber (220), having a first chamber volume in interruptible fluid communication with an external instrumentality (I) through an instrument aperture (210);
wherein the first movable plunger body (300) has at least one first plunger body sidewall (305) enclosing a second chamber (320) having a second chamber volume, and
the first variable chamber (220) is in fluid communication with the second chamber (320) by means of the fluid filtering barrier (310) such that fluid contained within the first variable chamber (220) may transit the fluid filtering barrier (310) into the second chamber; and
an attachable mixing chamber comprising at least one mixing chamber sidewall (505) enclosing a mixing chamber volume said mixing chamber attachable to said filtration syringe at said instrument aperture (210), and in fluid communication with the first variable chamber (220) through a mixing chamber-syringe aperture (520) and in fluid communication with the external instrumentality (I) through a mixing chamber-instrument aperture (510), wherein the mixing chamber sidewall (505) has at least one laminar flow disrupting feature (530).

2. The kit according to claim 1, wherein the instrument aperture (210) is reversibly occludable by an instrument aperture occluder (215).

3. The kit according to claim 2, wherein the instrument aperture occluder (215) is a removable cap.

4. The kit according to claim 2, wherein the instrument aperture occluder (215) is a valve allowing alternating bidirectional flow.

5. The kit according to claim 1, wherein the fluid filtering barrier (310) passes solids passable through a pore size of approximately between 5 and 50 microns.

6. The kit according to claim 1, wherein a chamber selected from the group of chambers consisting of the first variable chamber (220) and the second chamber (320) further contains a biologically active adjunct consisting of one or more of the adjuncts selected from the group of adjuncts consisting of cytokines, bone morphogenetic proteins (BMPs), pharmaceutical drugs, gene vectors or mixtures thereof.

7. The kit according to claim 1, wherein a chamber selected from the group of chambers consisting of the first variable chamber (220) and the second chamber (320) further contains a pigment selected from the group of pigments consisting of an anthocyanin, an anthocyanidin, or a combination of an anthocyanin and an anthocyanidin.

8. The kit according to claim 1, wherein the second chamber (320) is in interruptible fluid communication with an ambient atmosphere through an equalization aperture (330) that is reversibly occludable by an equalization aperture occluder (335).

9. The kit according to claim 8, wherein the equalization aperture occluder (335) is a valve allowing alternating bidirectional flow.

10. The kit according to claim 8, wherein the equalization aperture occluder (335) is a puncturable septum.

11. The kit according to claim 1, wherein the second chamber (320) further comprises an axially disposed movable second plunger body (400) having a fluid impermeable barrier (410) reversibly movable in an axial direction within the first plunger body (400) to enclose a second variable chamber (340) having a second variable chamber volume.

12. The kit according to claim 11, wherein the axially disposed movable second plunger body (400) may be biased to maintain a reversibly fixed position within the first plunger body (300) by means of a plunger interlock (440).

13. The kit according to claim 11, wherein the fluid filtering barrier (310) passes solids passable through a pore size of approximately between 5 and 50 microns.

14. The kit according to claim 11, wherein a chamber selected from the group of chambers consisting of the first variable chamber (220) and the second variable chamber (340) further contains a biologically active adjunct consisting of one or more of the adjuncts selected from the group of adjuncts consisting of cytokines, bone morphogenetic proteins (BMPs), pharmaceutical drugs, gene vectors or mixtures thereof.

15. The kit according to claim 11, wherein a chamber selected from the group of chambers consisting of the first variable chamber (220) and the second variable chamber (340) further contains a pigment selected from the group of pigments consisting of an anthocyanin, an anthocyanidin, or a combination of an anthocyanin and an anthocyanidin.

16. A kit comprising a filtration syringe (100) comprising, a syringe body (200) having a longitudinal axis (A) and at least one syringe body sidewall (205) cooperating with an axially disposed movable first plunger body (300) having a fluid filtering barrier comprised of a semipermeable membrane (310) movable within the syringe body (200) in an axial direction to enclose a first variable chamber (220), having a first chamber volume in interruptible fluid communication with an external instrumentality (I) through an instrument aperture (210);

wherein the first movable plunger body (300) has at least one first plunger body sidewall (305) enclosing a second chamber (320) having a second chamber volume, comprises an axially disposed movable second plunger body (400) having a fluid impermeable barrier (410) reversibly movable in an axial direction within the first plunger body (400) to enclose a second variable chamber (340) having a second variable chamber volume, and the first variable chamber (220) is in fluid communication with the second chamber (320) by means of the fluid filtering barrier (310) such that fluid contained within the first variable chamber (220) may transit the fluid filtering barrier (310) into the second chamber; and an attachable mixing chamber comprising at least one mixing chamber sidewall (505) enclosing a mixing chamber volume said mixing chamber attachable to said filtration syringe at said instrument aperture (210), and in fluid communication with the first variable chamber (220) through a mixing chamber-syringe aperture (520) and in fluid communication with the external instrumentality (1) through a mixing chamber-instrument aperture (510), wherein the mixing chamber sidewall (505) has at least one laminar flow disrupting feature (530) (320).

17. A kit comprising a filtration syringe (100) comprising, a syringe body (200) having a longitudinal axis (A) and at least one syringe body sidewall (205) cooperating with an axially disposed movable first plunger body (300) having a fluid filtering barrier comprised of a semipermeable membrane (310) movable within the syringe body (200) in an axial direction to enclose a first variable chamber (220), having a first chamber volume in interruptible fluid communication with an external instrumentality (I) through an instrument aperture (210);

wherein the first movable plunger body (300) has at least one first plunger body sidewall (305) enclosing a second chamber (320) having a second chamber volume, the first variable chamber (220) is in fluid communication with the second chamber (320) by means of the fluid filtering barrier (310) such that fluid contained within the first variable chamber (220) may transit the fluid filtering barrier (310) into the second chamber (320), and the second chamber (320) is in interruptible fluid communication with an ambient atmosphere through an equalization aperture (330) that is reversibly occludable by an equalization aperture occluder; and an attachable mixing chamber comprising at least one mixing chamber sidewall (505) enclosing a mixing chamber volume said mixing chamber attachable to said filtration syringe at said instrument aperture (210), and in fluid communication with the first variable chamber (220) through a mixing chamber-syringe aperture (520) and in fluid communication with the external instrumentality (1) through a mixing chamber-instrument aperture (510), wherein the mixing chamber sidewall (505) has at least one laminar flow disrupting feature (530) (335).

* * * * *